US011147610B2

United States Patent
Govari et al.

(10) Patent No.: US 11,147,610 B2
(45) Date of Patent: *Oct. 19, 2021

(54) TISSUE THICKNESS USING PULSED POWER

(71) Applicant: Biosense Webster (Israel) Ltd., Yokneam (IL)

(72) Inventors: Assaf Govari, Haifa (IL); Israel Zilberman, Yokneam (IL); Andres Claudio Altmann, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 577 days.

This patent is subject to a terminal disclaimer.

(21) Appl. No.: 15/657,270

(22) Filed: Jul. 24, 2017

(65) Prior Publication Data

US 2018/0228529 A1 Aug. 16, 2018

Related U.S. Application Data

(60) Provisional application No. 62/457,266, filed on Feb. 10, 2017, provisional application No. 62/470,983, filed on Mar. 14, 2017.

(51) Int. Cl.
*A61B 18/14* (2006.01)
*A61B 18/12* (2006.01)
(Continued)

(52) U.S. Cl.
CPC .......... *A61B 18/14* (2013.01); *A61B 18/1492* (2013.01); *A61B 5/1076* (2013.01);
(Continued)

(58) Field of Classification Search
CPC .......... A61B 2018/00738; A61B 2018/00791; A61B 2018/00773; A61B 18/14;
(Continued)

(56) References Cited

U.S. PATENT DOCUMENTS

2002/0052599 A1  5/2002  Goble
2002/0173784 A1*  11/2002  Sliwa, Jr. .......... A61B 17/22012
                                                          606/28
(Continued)

FOREIGN PATENT DOCUMENTS

WO    WO2007092860 A2   8/2007

OTHER PUBLICATIONS

U.S. Appl. No. 62/457,266, filed Feb. 10, 2017 and U.S. Appl. No. 62/470,983, filed Mar. 14, 2017.
(Continued)

*Primary Examiner* — Jaymi E Della
*Assistant Examiner* — Sean W Collins
(74) *Attorney, Agent, or Firm* — Notaro, Michalos & Zaccaria P.C.

(57) ABSTRACT

Catheterization is carried out by bringing an electrode that is disposed on a distal portion of a catheter into contact with tissue, wherein the electrode has an area that falls within a range of 0.01-25 mm². A power generator delivers pulses of radiofrequency power through the electrode to the tissue. While applying the pulses temperatures at the distal portion of the catheter are recorded. A rate of change of the temperatures is calculated and tissue thickness estimated based on the rate of change.

12 Claims, 6 Drawing Sheets

(51) Int. Cl.
*A61B 18/00* (2006.01)
*A61B 5/107* (2006.01)
*A61B 90/00* (2016.01)
*A61B 34/10* (2016.01)
*A61B 34/20* (2016.01)

(52) U.S. Cl.
CPC . *A61B 18/1206* (2013.01); *A61B 2018/00029* (2013.01); *A61B 2018/00351* (2013.01); *A61B 2018/00357* (2013.01); *A61B 2018/00577* (2013.01); *A61B 2018/00702* (2013.01); *A61B 2018/00738* (2013.01); *A61B 2018/00773* (2013.01); *A61B 2018/00791* (2013.01); *A61B 2018/00839* (2013.01); *A61B 2034/104* (2016.02); *A61B 2034/2051* (2016.02); *A61B 2090/064* (2016.02); *A61B 2090/065* (2016.02); *A61B 2218/002* (2013.01)

(58) Field of Classification Search
CPC . A61B 18/1492; A61B 5/1076; A61B 8/4263; A61B 8/429; A61B 2017/00243; A61B 2034/104; A61B 2218/002; A61B 2090/065; A61B 2018/00351; A61B 2018/00577; A61B 2018/00702; A61B 2018/00029; A61B 18/1206; A61B 2018/00357; A61B 5/05; A61B 5/01; A61B 8/12; A61B 2562/0271
See application file for complete search history.

(56) References Cited

U.S. PATENT DOCUMENTS

| | | |
|---|---|---|
| 2005/0256522 A1 | 11/2005 | Francischelli |
| 2006/0173251 A1 | 8/2006 | Govari |
| 2007/0038078 A1 | 2/2007 | Osadchy |
| 2008/0033425 A1* | 2/2008 | Davis ................ A61B 17/0057 606/41 |
| 2010/0113985 A1 | 5/2010 | Thapliyal, V |
| 2010/0191142 A1* | 7/2010 | Paul ..................... A61B 5/015 600/549 |
| 2011/0264087 A1 | 10/2011 | Haemmerich |
| 2014/0039489 A1* | 2/2014 | Davalos ................ A61N 1/327 606/34 |
| 2014/0266235 A1* | 9/2014 | Mathur ................ G01R 31/50 324/509 |
| 2015/0272667 A1 | 10/2015 | Govari |
| 2016/0166309 A1* | 6/2016 | K V ...................... A61B 34/25 606/32 |
| 2016/0183915 A1 | 6/2016 | Govari |
| 2017/0014181 A1 | 1/2017 | Bar-Tal |
| 2017/0112405 A1 | 4/2017 | Sterrett |

OTHER PUBLICATIONS

European Search Report for corresponding EPA No. 18184989.4 dated Dec. 10, 2018.
Rozen Guy et al.., "Prediction of radiofrequency ablation lesion formation using a novel temperature sensing technology incorporated in a force sensing catheter", Heart Rhythm, vol. 14, No. 2, Jan. 16, 2017, pp. 248-254.

* cited by examiner

TISSUE THICKNESS USING PULSED POWER

CROSS-REFERENCE TO RELATED APPLICATIONS

This Application claims the benefit of U.S. Provisional Application No. 62/457,266, filed 10 Feb. 2017, entitled Estimation of Tissue Thickness and 62/470,983, filed 14 Mar. 2017, entitled Estimation of Tissue Thickness from Rate of Change of Catheter Temperature, which are herein incorporated by reference.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to medical instruments. More particularly, this invention relates to medical instruments for measuring thickness of a tissue layer that are actuated by application of energy.

2. Description of the Related Art

Invasive and non-invasive techniques have been used to assess tissues within the body. These techniques are particularly relevant to medical procedures in which is necessary to know the relationships of certain tissues to other tissues and to organs that are subject to injury from instruments such as ablation catheters, biopsy needles and the like. For example, cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

A known difficulty in the use of radiofrequency energy for cardiac tissue ablation is controlling local heating of tissue. There are tradeoffs between the desire to create a sufficiently large lesion to effectively ablate an abnormal tissue focus, or block an aberrant conduction pattern, and the undesirable effects of excessive local heating. If the radiofrequency device creates too small a lesion, then the medical procedure could be less effective, or could require too much time. On the other hand, if tissues are heated excessively then there could be local charring effects, coagulum, and or explosive steam pops due to overheating. If the radiofrequency device creates too large a lesion adjacent tissue can be inadvertently ablated. In some cases, perforation of the wall of the heart could occur. It is therefore desirable to know the thickness of the tissue being ablated.

In a number of cases this may be deduced from a pre-acquired image of the tissue, such as from an MRI (magnetic resonance imaging) or a CT (computerized tomography) image. In the case of ablation, this data may not be available to the professional performing the ablation. Even if it is available, it may not give the thickness to sufficient accuracy, or the thickness may have changed since acquisition of the image.

Commonly assigned U.S. Patent Application Publication No. 20160183915 by Govari et al., which is herein incorporated by reference, describes tissue thickness measurement using ultrasound, by determining the period for an ultrasound pulse from a transducer to be reflected back to the transducer (in the A-mode of operation of the transducer). Background noise is eliminating by placing the transducer in contact with the tissue, and moving the distal tip vertically, i.e., normal to the tissue surface, back and forth, thereby compressing are decompressing the tissue. The vertical motion causes the pulses to return at different periods, because of the differing distances of the tissue traversed by the pulses. Contact force is correlated with the signals acquired by the transducer, in order to isolate pulses returning from a tissue interface of interest from background reflections and noise. The correlation may use the fact that the returning pulse period at a high force is less than the returning pulse period at a low force, since the actual tissue thickness is smaller for the high force situation compared to the low force situation.

SUMMARY OF THE INVENTION

Embodiments of the present invention provide an independent measure of the thickness of tissue being investigated. For an ablation procedure the method may be applied while ablation is actually being performed, or while no ablation is occurring. The measure relies on the discovery by the inventor that if a heat energy pulse is injected into tissue from the distal end of a catheter in contact with the tissue, the rate of change of the temperature of the distal end varies according to the thickness of the tissue. For thick tissue the rate is large, and for thin tissue the rate is small.

Thus, in a typical procedure using radiofrequency energy for ablating tissue, a catheter distal end is inserted into proximity with the tissue to be ablated, and the distal end and the tissue are irrigated at a given rate. During the irrigation a radiofrequency pulse is applied for a short time to the tissue, and the temperature of the catheter distal end, typically a mean temperature calculated from multiple sensors in the distal end, is monitored. The thickness of the tissue is then estimated from the measured rate of change of the temperature of the distal end. The estimation typically comprises using a relationship between a normalized rate of change of the temperature of the distal end and the thickness of the tissue. The relationship may be determined prior to insertion of the catheter into proximity with the tissue.

Once the tissue thickness has been estimated, the value of the thickness may be used in estimating the power to be used for the ablation, and the time period over which the power is to be applied, in order to achieve a successful ablation of the tissue.

There is provided according to embodiments of the invention a method, which is carried out by bringing an electrode that is disposed on a distal portion of a catheter into contact with tissue, wherein the electrode has an area that falls within a range of 0.01-25 mm². The method is further carried out by applying pulses of radiofrequency power through the electrode to the tissue, the pulses having a width of between 10 µs and 100 µs. The method is further carried out while applying the pulses by recording temperatures at the distal portion, computing a rate of change of the temperatures at the distal portion, and making an estimate of a thickness of the tissue in response to the rate of change.

According to one aspect of the method, the area of the electrode does not exceed 2.8 mm².

According to an aspect of the method, recording temperatures is performed at times corresponding to terminations of the pulses.

According to yet another aspect of the method, the width of the pulses is 100 µs.

According to a further aspect of the method, the pulses are iterated between 10 to 100 times per second.

According to an additional aspect of the method, the pulses are iterated 10 times per second.

According to another aspect of the method, the pulses have a power level of 1-10 W per mm² of electrode area.

According to yet another aspect of the method, the power level is 10 W per mm² of electrode area.

One aspect of the method includes determining a relationship between the rate of change, the thickness of the tissue, a level and a time of the pulses, and an irrigation rate for irrigating the tissue. The relationship is used to estimate the thickness of the tissue.

Still another aspect of the method includes using the estimate to ablate the tissue at a depth that is calculated according to an ablation index.

There is further provided according to embodiments of the invention an apparatus, including a catheter, an electrode disposed on the distal portion of the catheter, wherein the electrode has an area that falls within a range of 0.01-25 mm². The apparatus includes a power generator connected to the electrode and configured to apply pulses of radiofrequency power to tissue in contact with the electrode, the pulses having a width of between 10 µs and 100 µs. A temperature sensor at the distal portion records temperatures while the pulses are being applied, and a processor is operative for computing a rate of change of the temperatures at the distal portion in response to the recorded temperatures and for making an estimate of a thickness of the tissue in response to the rate of change.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 1:
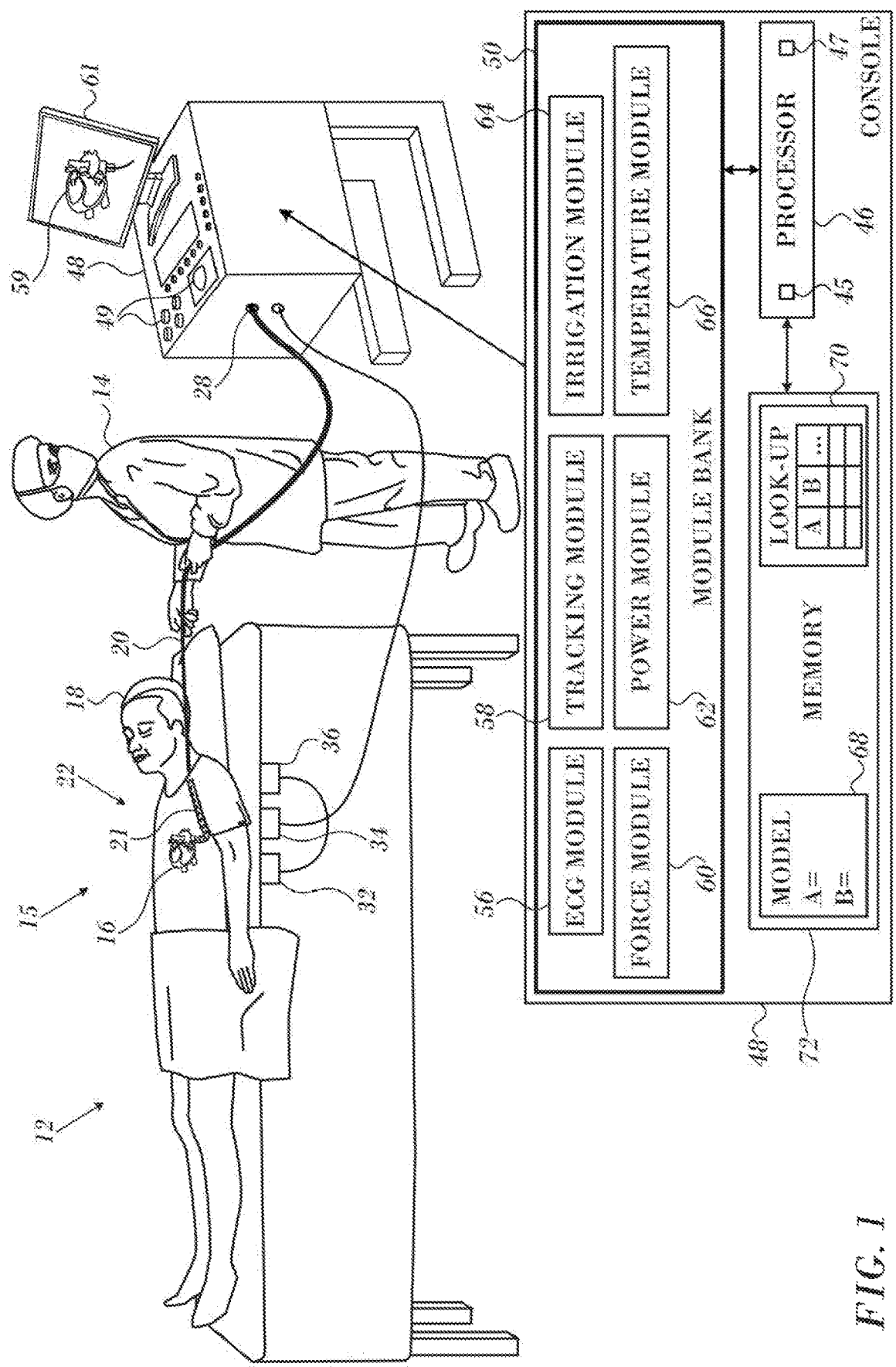
FIG. 1 is a schematic illustration of an invasive medical procedure using apparatus, according to an embodiment of the present invention.
Figure 2:
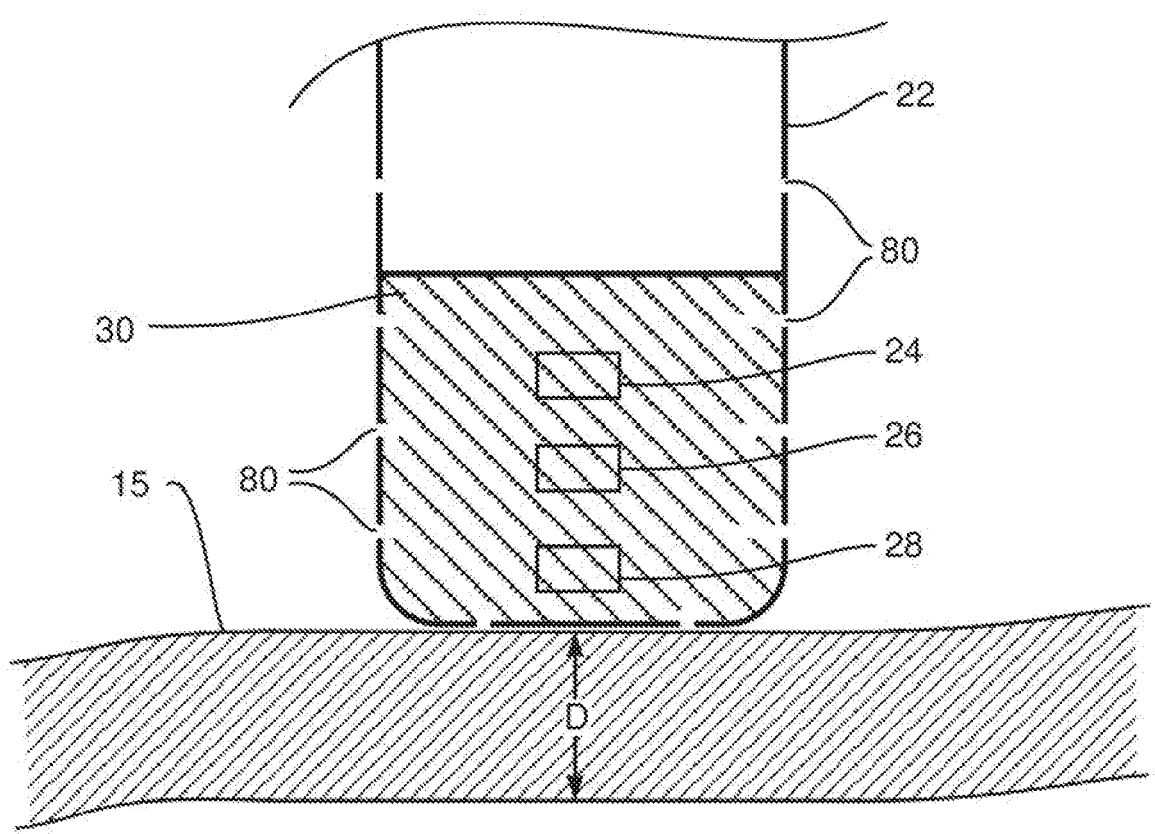
FIG. 2 is a schematic illustration of a distal end of a probe used in the apparatus, according to an embodiment of the present invention.

Turning now to the drawings, reference is initially made to FIG. 1, which is a schematic illustration of an invasive medical procedure using apparatus 12, and to FIG. 2, which is a schematic illustration of a distal end 22 of a catheter or probe 20 used in the apparatus, according to an embodiment of the present invention. The procedure is performed by a medical professional 14, and in the description hereinbelow the procedure is assumed to comprise an ablation of a portion of tissue 15 of a myocardium 16 of the heart of a human patient 18.

In order to perform the investigation, professional 14 inserts probe 20 into a sheath 21 that has been pre-positioned in a lumen of the patient. Sheath 21 is positioned so that distal end 22 of the probe enters the heart of the patient. Distal end 22 comprises a position sensor 24 that enables the location and orientation of the distal end to be tracked, a force sensor 26 that measures the force applied by the distal end when it contacts the myocardium, and one or more temperature sensors 28 that measure the temperature at respective locations of the distal end. Distal end 22 also comprises an electrode 30, which is used to deliver radiofrequency ablation power to myocardium 16 in order to ablate the myocardium. Electrode 30 may also be used to acquire electropotentials from the myocardium, as noted below.

Apparatus 12 is controlled by a system processor 46, which is located in an operating console 48 of the apparatus. Console 48 comprises controls 49, which are used by professional 14 to communicate with the processor 46. The software for processor 46 may be downloaded to the processor in electronic form, over a network, for example. Alternatively or additionally, the software may be provided on non-transitory tangible media, such as optical, magnetic, or electronic storage media. The track of distal end 22 is typically displayed on a three-dimensional representation 59 of the heart of patient 18 that is displayed on a screen 61.

System processor 46 comprises real-time noise reduction circuitry 45, typically configured as a field programmable gate array (FPGA), followed by an analog-to-digital (A/D)) signal conversion integrated circuit 47. The processor can pass the signal from A/D circuit 47 to another processor and/or can be programmed to perform at least one algorithm disclosed herein, the algorithm comprising steps described hereinbelow. The processor uses circuitry 45 and circuit 47, as well as features of modules, which are described in more detail below, in order to perform the algorithm.

In order to operate apparatus 12, the algorithm of processor 46 communicates with a module bank 50, which has a number of modules used by the processor to operate the apparatus. Thus, bank 50 comprises an electrocardiograph (ECG) module 56, which acquires and analyzes signals from electrode 30, and a tracking module 58, which receives and analyzes signals from position sensor 24, and which uses the signal analysis to generate a location and an orientation of distal end 22. In some embodiments position sensor 24 comprises one or more coils, which provide the sensor signals in response to magnetic fields traversing the coils. In these embodiments, in addition to receiving and analyzing signals from sensor 24, tracking module 58 also controls radiators 32, 34, 36, which radiate the magnetic fields traversing position sensor 24. The radiators are positioned in proximity to myocardium 16, and are configured to radiate alternating magnetic fields into a region in proximity to the myocardium. The Carto® system produced by Biosense Webster, of Diamond Bar, Calif., uses such a magnetic tracking system.

Bank 50 also comprises a force module 60, a power module 62, an irrigation module 64, and a temperature module 66. The functions of these modules are explained below.

Force module 60 receives signals from force sensor 26, and from the signals generates a magnitude CF of the contact force, herein assumed to be measured in grams, exerted by distal end 22 on tissue 15. In some embodiments the force sensor 26 is configured so that the signals it provides to force module 60 enable the module to evaluate a direction of the force exerted by the distal end on tissue 15.

Power module 62 generates the radiofrequency power that is conveyed to electrode 30, and that is applied by the electrode to ablate tissue 15. Processor 46 and power module 62 are able to adjust a power level P, herein assumed to be measured in Watts, delivered by the electrode, as well as a length of time t, measured in seconds, during which the power is delivered, as described in more detail below.

Irrigation module 64 controls a rate of flow V, herein assumed to be measured in mL/min, of irrigation fluid, typically normal saline solution, supplied to distal end 22. The irrigation fluid is expelled from irrigation holes 80 in the distal end.

Temperature module 66 receives signals from one or more temperature sensors 28, and determines the temperatures registered by each of the sensors. Typically, in the case of multiple temperature sensors 28 the module determines a mean temperature T of distal end 22. Additionally, in the case of multiple sensors, the module may produce a map of the temperature distribution of the distal end.

The inventor has found that on injection of a heat energy pulse into tissue 15 an overall thickness D of the tissue affects the rate of change of temperature $$\frac{\Delta T}{\Delta t}$$

measured by one or more temperature sensors 28. In particular, for a given irrigation rate V of fluid through the distal end, and for a given contact force CF applied to the tissue by the distal end, the rate of change of temperature $$\frac{\Delta T}{\Delta t}$$

is large for large values of D and is small for small values of D. The heat energy pulse may be injected into the tissue by applying radiofrequency power for a short time to the tissue. The inventor believes that the relationship described above, between the rate of change of temperature $$\frac{\Delta T}{\Delta t}$$

and the overall tissue thickness D, is due to the heat energy retained by the tissue, i.e., tissue having a large value D retains more heat energy than tissue having a small value D.

The relationship may be expressed by the following equation (1):

$$D = f\left(\frac{\Delta T}{\Delta t}\right) \qquad (1)$$

where D is the thickness of the tissue,
ΔT is the change of temperature of the distal end in a time period Δt, and
f is a function.

In one embodiment, the function f is as given in equation (2):

$$D = A\left(1 - e^{-\frac{s}{B}}\right)^n \qquad (2)$$

where
n is a numerical exponent,
A, B are constant parameters having values, which depend on the thermal characteristics of the distal end of the catheter,
and
s is a normalized slope of a temperature-time graph, i.e., $$s = \left[\frac{\Delta T}{\Delta t}\right]_{NORM} \qquad (2a)$$

The non-normalized slope of the temperature-time graph, $$\frac{\Delta T}{\Delta t},$$

depends on the contact force CF applied by the distal end to the tissue, the level P of the radiofrequency pulse power applied, the length of time t of application of the radiofrequency power pulse, and the irrigation rate V.

The non-normalized slope, $$\frac{\Delta T}{\Delta t},$$

is converted to a normalized slope, $$\left[\frac{\Delta T}{\Delta t}\right]_{NORM}$$

by normalizing CF to a normalized contact force $CF_{NORM}$, P to a normalized pulse power $P_{NORM}$, t to a normalized a pulse length $t_{NORM}$, and V to a normalized irrigation rate $V_{NORM}$. The normalization assumes respective relationships between the non-normalized slope and the contact force CF, the P pulse power P applied, the pulse length t, and the irrigation rate V. In an embodiment the relationships for CF, P, and t are assumed to comprise respective direct proportionalities, and the relationship for V is assumed to comprise an inverse proportionality. However, other relationships that may be used in normalizing the slope of the temperature-time graph will be apparent to those having ordinary skill in the art, and all such relationships are assumed to be comprised within the scope of the present invention.

In an embodiment the numerical exponent n in equation (2) is set as 1 or 2. In other embodiments the value for n may be set to be different from 1 and 2, and may be a non-integer value.

Values of A and B, as well as the normalized values referred to above, and values of the parameters of the relationships for normalizing the slope $$\frac{\Delta T}{\Delta t},$$

may be stored as a model 68 and/or in a look-up table 70 contained in a memory 72 that is accessed by processor 46.

Figure 3:
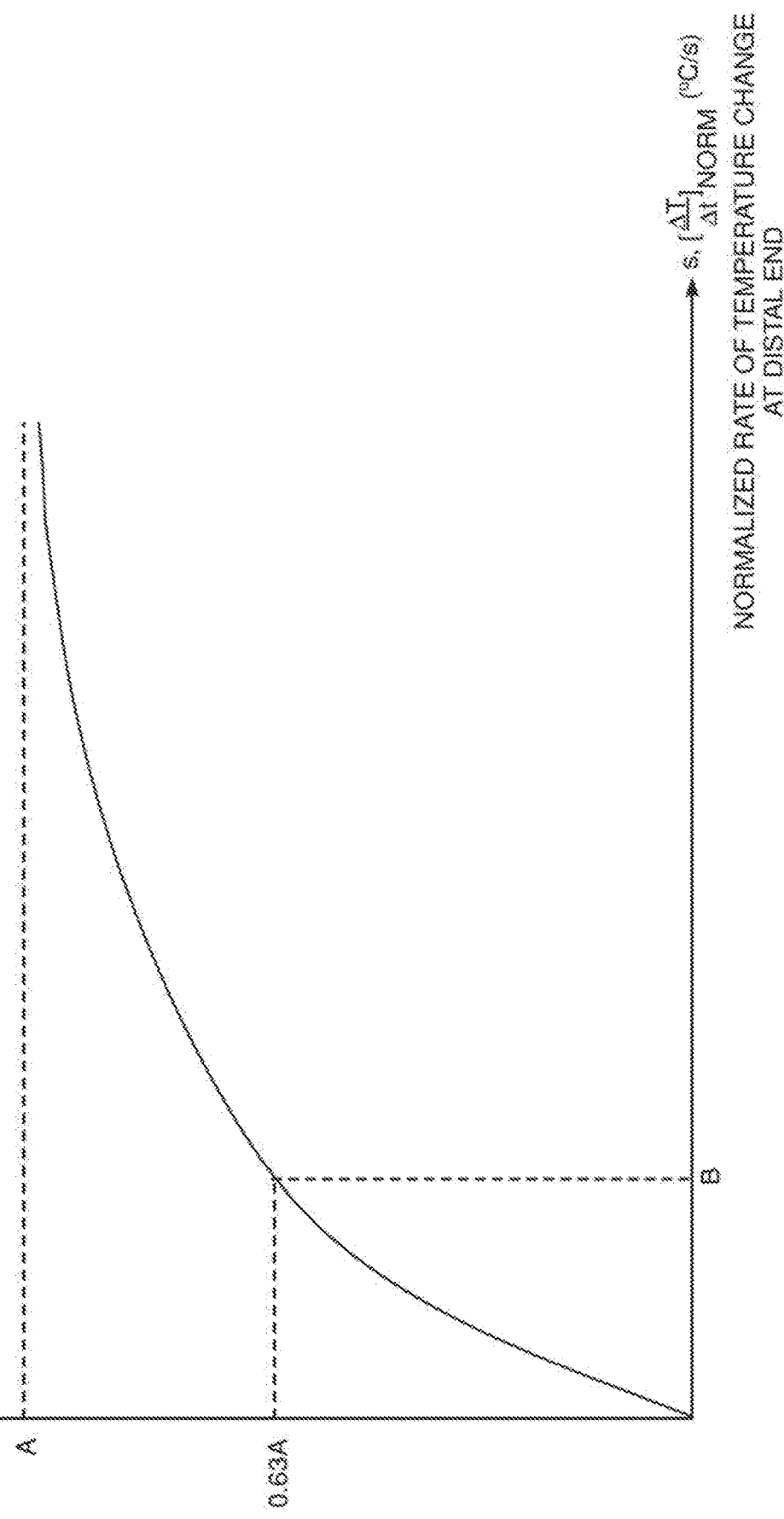
FIG. 3 is a schematic graph of tissue thickness vs. slope, according to an embodiment of the present invention.

Reference is now made to FIG. 3, which is a schematic graph of thickness D vs. normalized slope s, as determined from equation (2), for n=1, according to an embodiment of the present invention. As is illustrated in the graph, the slope s, $$\left[\frac{\Delta T}{\Delta t}\right]_{NORM}$$

increases monotonically with respect to the tissue thickness D. As is also illustrated, the graph exponentially approaches an asymptote D=A as the slope s increases.

For clarity and simplicity, except where otherwise stated, the following description assumes that the relationship between the tissue thickness and the rate of change of temperature is as given by equation (2) with n=1. Those having ordinary skill in the art will be able to modify the description, mutatis mutandis, for other values of n and for other relationships of the form of equation (1).

Prior to performing an actual ablation procedure, professional 14 may determine values for A and B in equation (2), as well as values for the relationships used for normalizing the slope $$\frac{\Delta T}{\Delta t},$$

by ablation of tissue using measured values of tissue thickness D and slope $$\frac{\Delta T}{\Delta t}.$$

Typically such a determination involves using a range of values of irrigation rate V, radiofrequency pulse power P, length of time t of the pulse, and contact force CF. The values of P, V, and t are typically chosen so that the temperature of the tissue being used remains within a range of approximately 40° C.-60° C., so that any change of temperature is not harmful to the tissue.

In one embodiment the values for V are set within a range 10-20 mL/min, the values of P are set within a range of 20-30 W, the pulse length t is set within a range of 1-3 s, the contact force CF is within a range of 5-25 grams, and the normalized values are set at $V_{NORM}$=15 mL/min, $P_{NORM}$=25 W, $t_{NORM}$=2 s, and $CF_{NORM}$=15 grams. However, providing that the temperature of the tissue being used remains between approximately 40° C.-60° C., V, P, and t may have values outside these ranges, and the normalized values may be different from those provided here, and such alternative values may be determined by one with ordinary skill in the art without undue experimentation.

To determine A and B for a selected catheter, the distal end of the catheter is brought into contact with tissue of a known thickness D, and the distal end is configured to exert the normalized contact force $CF_{NORM}$ on the tissue while the distal end and tissue are irrigated at the normalized irrigation rate $V_{NORM}$. A radiofrequency pulse with the normalized power $P_{NORM}$ and pulse length $t_{NORM}$ is applied to the tissue, and the temperature T of the distal end is recorded as it changes over time. From the recordation of the distal end temperatures and times, an estimate of the normalized slope, $$\left[\frac{\Delta T}{\Delta t}\right]_{NORM},$$

is made. In one embodiment the value of $$\left[\frac{\Delta T}{\Delta t}\right]_{NORM}$$

is calculated from the change of temperature ΔT for a value of Δt of 5 s, where the value Δt is taken over the first 5 s of recordation.

The above determination is repeated for different values of tissue thickness D, giving respective different values of $$\left[\frac{\Delta T}{\Delta t}\right]_{NORM}$$

to get A and B values for the selected catheter.

For each selected catheter professional 14 may use processor 46 to store the respective values of A, B, as mathematical model 68 (FIG. 1). Model 68 is a mathematical function, such as a cost function, that enables the processor to determine values of A and B from the experimental values of V, P, t and CF, together with values for the respective normalizing relationships to the normalized values $V_{NORM}$, $P_{NORM}$, $t_{NORM}$ and $CF_{NORM}$, as described above. Alternatively or additionally, professional 14 may configure the processor to store the respective values of A and B for each selected catheter, as well as the values for the respective relationships in look-up table 70.

Figure 4:
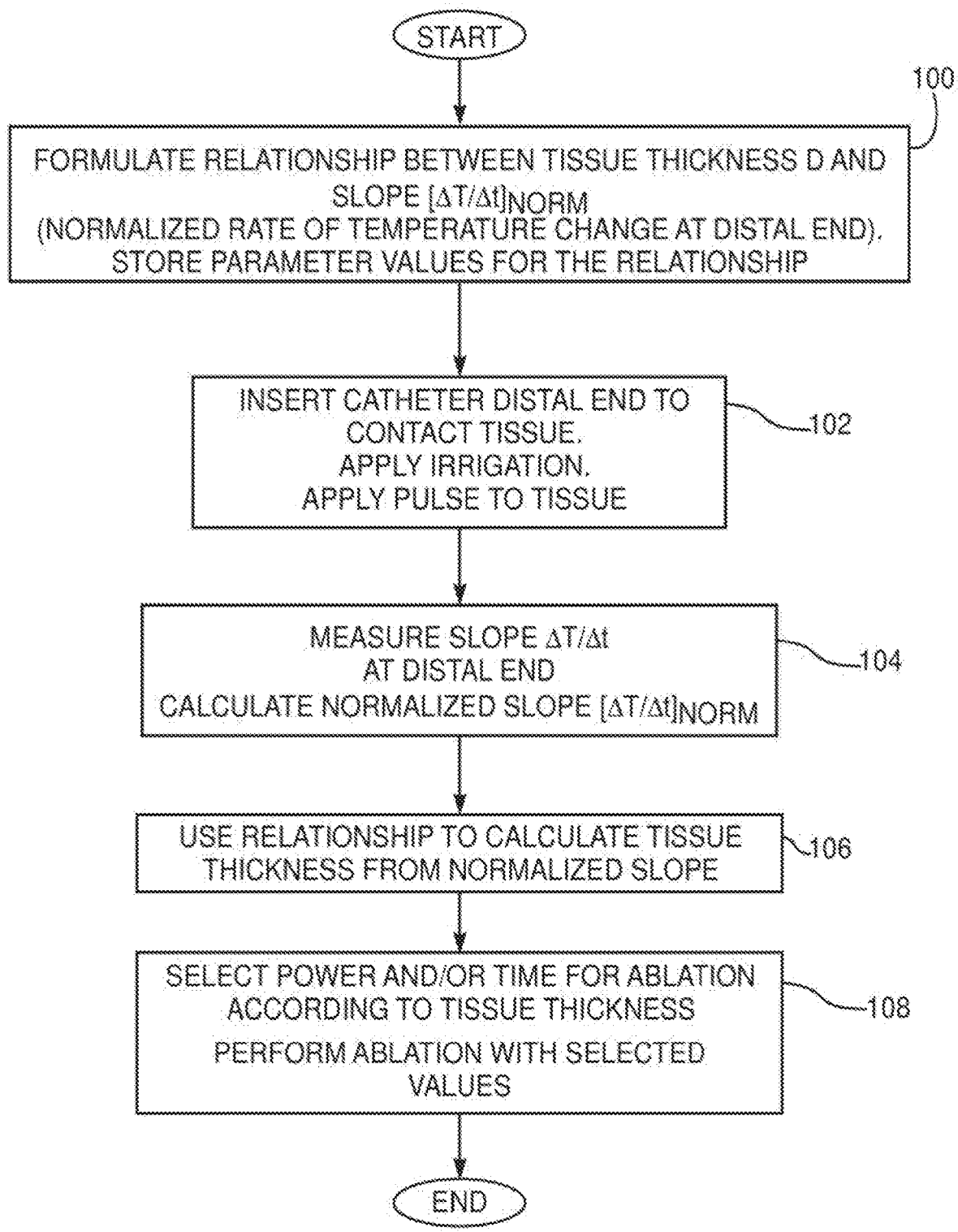
FIG. 4 is a flowchart of steps followed by a professional in performing the procedure, according to an embodiment of the present invention.

Reference is now made to FIG. 4, which is a flowchart of steps followed by professional 14 and the algorithm of processor 46 in performing the ablation procedure referred to above, according to an embodiment of the present invention. In a preparatory step 100 that is typically performed before the start of the ablation procedure, the relationship between tissue thickness D and normalized slope s, i.e., the normalized rate of temperature change $$\left[\frac{\Delta T}{\Delta t}\right]_{NORM}$$

of distal end 22, is formulated. As stated above, for simplicity and clarity the relationship herein is assumed to correspond to equation (2) with n=1. In addition to formulating the relationship, in step 100 values for parameters of the relationship, in this case A and B, as well as parameters for the normalizing relationships are stored as look-up table 70 and/or mathematical model 68, as described above. Typically, a catheter having a distal end similar to the distal end 22 that is used in the ablation procedure of the present flowchart is used to perform the evaluations and/or generate look-up table 70 and mathematical model 68.

In an initial procedure step 102, professional 14 inserts distal end 22 to contact a selected portion of tissue 15 of myocardium 16, and force module 60 and processor 46 record a contact force CF sensed by force sensor 26. Once in contact with tissue 15, the professional sets a flow rate V of irrigation to the distal end. Typically, the value for V is set within a range 10-20 mL/min, but V may have a value outside this range. In addition, while the distal end and the tissue are being irrigated, the processor uses electrode 30 to apply a radiofrequency power pulse to the tissue in contact with the distal end. In one embodiment the processor sets the pulse to have a power P of 30 Watts and a duration t of 1 second. The processor records the values of V, P, and t.

In a slope measurement step 104, once the pulse has been applied to tissue 15, the processor begins recording the temperature of the one or more temperature sensors 28, as well as the times of recordation. From the temperatures and the times, the processor evaluates a value of the slope $$\frac{\Delta T}{\Delta t}.$$

From the slope, the processor calculates the normalized rate of temperature change $$\left[\frac{\Delta T}{\Delta t}\right]_{NORM},$$

i.e., the normalized slope of the corresponding temperature-time graph, of distal end 22.

In a tissue thickness step 106, the processor applies the normalized slope found in step 104 to the relationship formulated in step 100, together with appropriate values for parameters A, B, of the relationship, to evaluate a thickness D of tissue 15. For the relationship corresponding to equation (2) with n=1, the values of A and B are found from look-up table 70 and/or mathematical model 68.

In an ablation step 108 the processor uses the evaluated tissue thickness D to estimate a radiofrequency power P and a duration time t for which the power is to be applied, to ablate tissue 15. The estimation typically uses an ablation index, described below.

As is known in the art, an ablation index is a function, having a value that changes as ablation proceeds, which provides an estimate of the size of a lesion produced by the ablation of a tissue of known type. The estimate provided by the index depends on the values of the contact force CF and power P measured during the ablation, as well as on the period of time of the ablation. Ablation indices are described in an article entitled "Ablation Index-guided Pulmonary Vein Isolation for Atrial Fibrillation may Improve Clinical Outcomes in Comparison to Contact Force-guided Ablation" to Hussein et al., presented at the 2016 Heart Rhythm Congress, and in U.S. Patent Application 2017/0014181 to Bar-Tal et al. Both documents are incorporated herein by reference.

Equation (3) below gives an expression for an ablation index:

$$D = (C\int_0^t CF^\alpha(\tau) P^\beta(\tau) d\tau)^\delta = \text{Ablation Index} \quad (3)$$

where C is a constant having a value depending on the type of tissue being ablated; in one embodiment C has an approximate value of 0.002, $\alpha$ is an exponent having a value typically in the range 0.6-0.8, $\beta$ is an exponent having a value typically in the range 1.4-1.8, $\delta$ is an exponent having an approximate value of 0.35, and D is an estimate of the depth of a lesion achieved by ablating for a time t, with instantaneous contact force CF($\tau$) and instantaneous power P($\tau$), and where T represents a time variable.

If the contact force and the power are assumed to be constant, having respective values $\overline{CF}$ and $\overline{P}$ during an ablation procedure that is to take a time t, then equation (3) may be rewritten as equation (4):

$$D = (C\overline{CF}^\alpha \overline{P}^\beta t)^\delta \quad (4)$$

The value of the left side of equation (4), tissue thickness D, is known from step 106. Processor 46 may thus use the right side of equation (4) to provide to professional 14 recommended values of power P and time t for ablation using the measured value of force CF and an estimate of C.

In step 108 professional 14 selects one of the recommended values of power P and time t to ablate tissue 15, and concludes the ablation of tissue 15 with these values.

The description above of steps of the flowchart assumes that professional 14 uses an ablation index in determining values of power to be applied during an ablation procedure. The ablation index may be calculated and the ablation power adjusted automatically by the processor. The ablation index acts as an aid to the professional in deciding values of parameters, such as power and time period of ablation, to be used during an ablation procedure. However, it will be understood that the professional may not use an ablation index in deciding values of such parameters, while still using the description of tissue thickness step 106 to estimate the thickness of tissue being ablated, and may adapt the flowchart description, mutatis mutandis, for such a case. It will thus be understood that the scope of the present invention includes cases where an ablation index is not used.

The description above has also assumed that the rate of change of temperature of the catheter distal end, i.e., the slope of the temperature-time graph, is normalized. Nevertheless, those having ordinary skill in the art will be able to adapt the description to accommodate cases where the rate of change of temperature of the catheter distal end is not normalized.

Ablation Circuitry.

Figure 5:
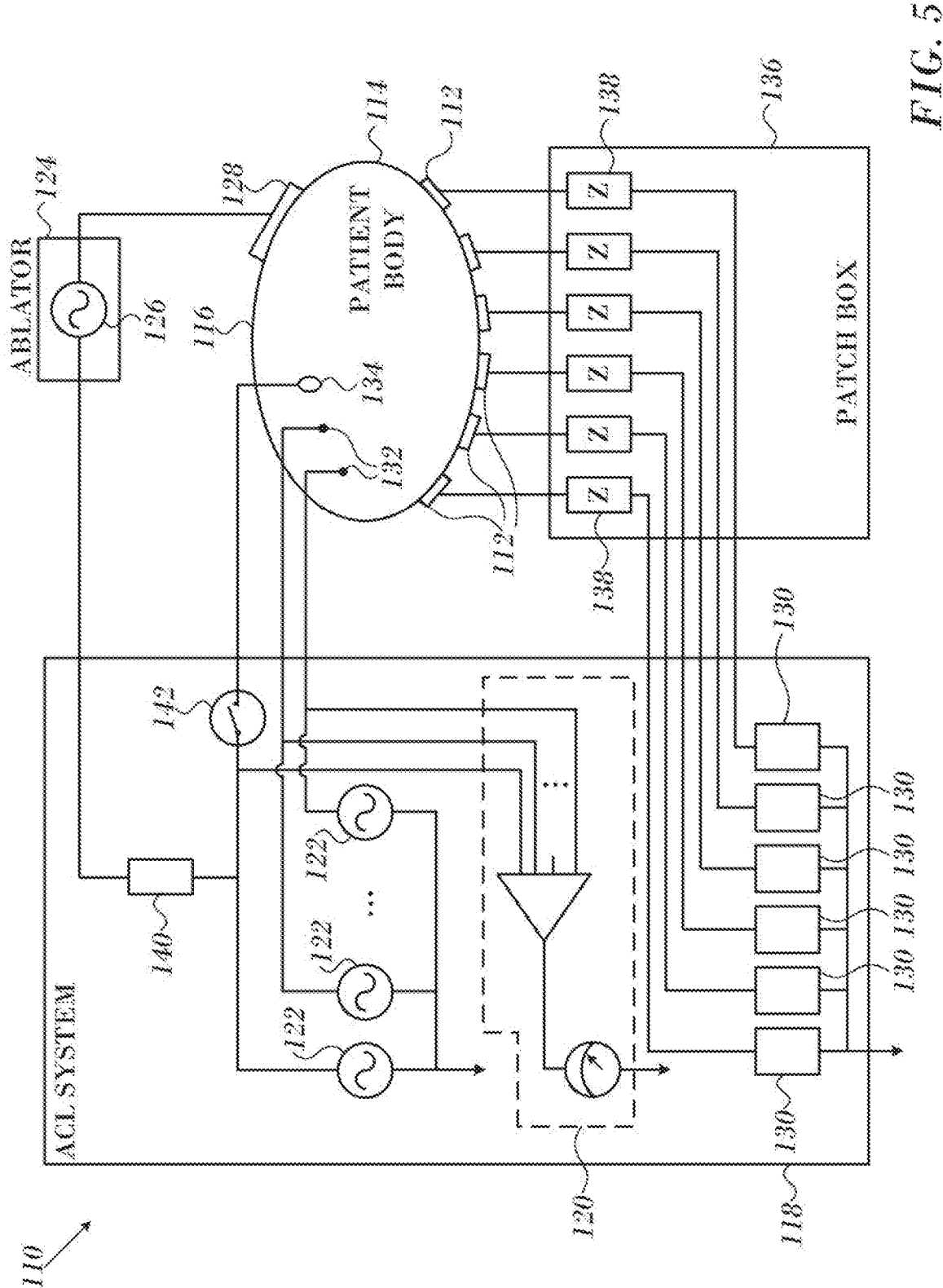
FIG. 5 is a schematic diagram of an ablation and active current location (ACL) circuit in accordance with an embodiment of the invention.

Reference is now made to FIG. 5, which is a schematic diagram of an ablation and active current location (ACL) circuit 110 for use with the system shown in FIG. 1. This arrangement is similar to that described in U.S. Patent Application Publications 2006/0173251, to Govari et al., and 2007/0038078, to Osadchy, which are herein incorporated by reference. The arrangement can be modified to operate in accordance with the principles of the present invention. A brief description follows for convenience of presentation.

A plurality of body surface electrodes 112, which can be adhesive skin patches, are coupled to a body surface 114 (e.g., the skin) of subject 116. The body surface electrodes 112 are sometimes referred to herein as "patches". In cardiac applications the body surface electrodes 112 are usually distributed so as to surround the heart, three on the chest of the subject and three on the back. However, the number of the body surface electrodes 112 is not critical, and they may be placed at convenient locations on the body surface 114 in the general vicinity of the site of the medical procedure.

A control unit 118, normally disposed in the console 24 (FIG. 1), includes current measurement circuitry 120 and one or more catheter electrode transmitters 122 for driving a current through one or more of the electrodes 112 to one or more of the body surface electrodes 112 at respective working frequencies. The control unit 118 is linked to a positioning processor (FIG. 1). The control unit 118 is linked to an ablator 124, which comprises at least one ablation generator 126. Currents through the body surface electrodes 112 and an ablator body surface electrode 128 flow in a circuit with the ablation generator 126 and are measured by respective current measurement circuits that are disposed within body electrode receivers 130, sometimes referred to herein as "patch measurement circuits". The body electrode receivers 130 are typically incorporated in the control unit 118. Alternatively, they may be affixed to the body surface electrodes 112. Catheter electrodes are represented in FIG. 5 as measurement electrodes 132 (circles) and a dual-purpose electrode 134 (ellipse). The dual-purpose electrode 134 functions as an ablation electrode and also serves as one of the measurement electrodes.

The body surface electrodes 112 are connected to the body electrode receivers 130 via a patch box 136, which protects the system from ablation and defibrillation currents. Typically the system is configured with six body electrode receivers 130. The patch box parasitic impedances 138 (Z), are measured during production and thus known a priori. These impedances are discussed below.

Typically, although only two measurement electrodes 132 are shown for convenience, about 80 measurement electrodes are used for impedance measurements. Typically there are one or two ablation electrodes. The coordinates of a catheter inside the body are determined in the positioning system by passing currents between electrodes on the catheter and the body surface electrodes 112.

The control unit 118 may also control an ablation circuit, comprising ablator 124, and the dual-purpose electrode 134. The ablator 124 is typically disposed externally to the control unit 118 and incorporates the ablation generator 126. It connects with the ablator body surface electrode 128 and to an ablator filter 140, which in this example is shown within the control unit 118. However this location is not essential. A switch 142 configures the ablator circuit for different modes of operation as described below. Voltage measurement circuitry is provided for determining the output of the catheter electrode transmitters 122. It will be noted from inspection of FIG. 5 that the ablation circuit is connected to one of the catheter electrode transmitters 122.

First Alternate Embodiment

Ablation requires relatively large electrodes to transfer sufficient radiofrequency (RF) energy from the catheter to the tissue so generate the sufficiently large heat pulse required for ablation, or for tissue thickness measurement as described above. Small electrodes, which are appropriate for non-ablation procedures, only support small amounts of RF energy transfer. In this case the heat pulse used for ablation electrodes is too small, and the catheter temperature rise is lost in the noise of the temperature sensor. Using this embodiment tissue thickness can be measured using catheters that lack ablation electrodes, e.g., mapping catheters.

Embodiments of the invention overcome the limited RF energy transfer capabilities of small electrodes by repeatedly injecting short pulses (pulse widths of 10-100 μs) of power P into the tissue, and averaging the temperature rise at the catheter to find $\Delta T$. By only using short pulses, there is basically no limitation on the size of the electrode used to inject the pulses, so that, for example, a small mapping electrode can be used. The averaging overcomes the noise problem, and a prior calibration is used to find the tissue thickness from the values of P and $\Delta T$. A typical size range for such electrodes is 1-4.8 $mm^2$, with typical power levels of 1-20 $W/mm^2$ at 10 pulses/sec.

Second Alternate Embodiment

In this embodiment microelectrodes are used to determine tissue thickness using the principles described above. In some embodiments, the microelectrodes can have a longitudinal length in a range from 0.1 to 5 millimeters and can have a lateral width in a range from 0.1 to 5 millimeters. However, in some embodiments, the microelectrodes can have a longitudinal length of approximately 0.92 millimeters and can have a lateral width of approximately 0.9 millimeters. In still other embodiments, the microelectrodes can have a longitudinal length of approximately 0.92 millimeters and a lateral width of approximately 0.3 millimeters. In yet other embodiments the microelectrodes can be circular, with a diameter of approximately 0.3-0.5 mm. Catheters having microelectrodes that are suitable for determination of tissue thickness using the principles of the invention are disclosed in commonly assigned U.S. Patent Application Publication No. 2015-0272667, entitled Temperature Measurement in Catheter, by Govari et al., which is herein incorporated by reference, and U.S. Patent Application Publication No. 20170112405, entitled High Density Mapping Catheter.

EXAMPLES

Figure 6:
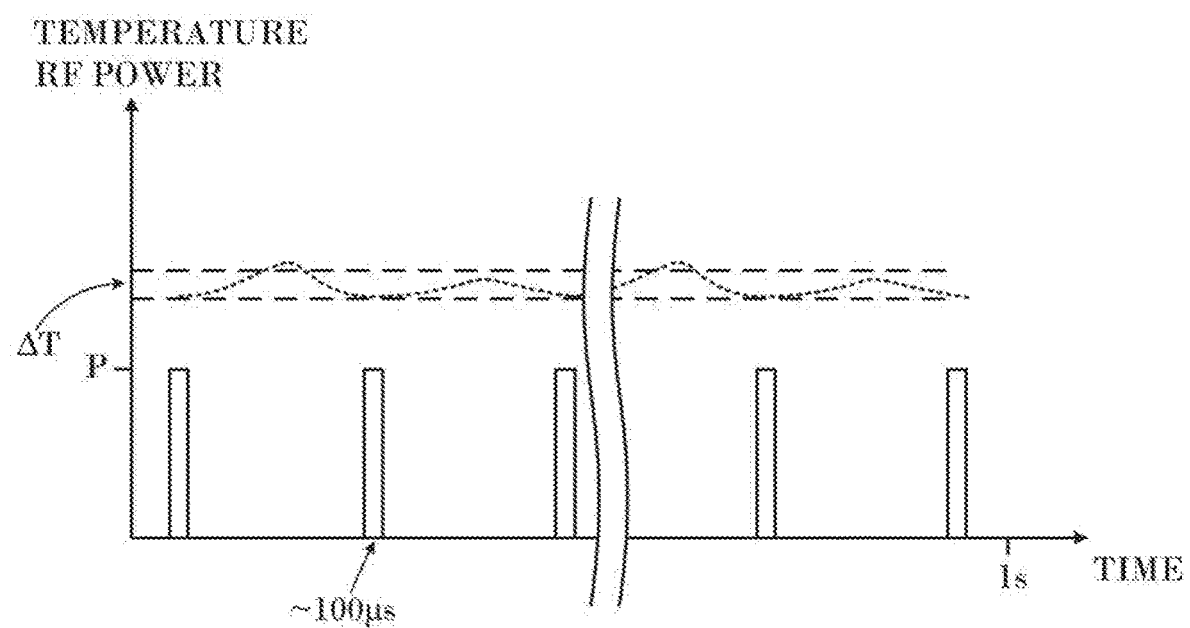
FIG. 6 is a plot of the change of temperature ΔT over time in tissue in accordance with an embodiment of the invention.

Reference is now made to FIG. 6, which is a plot of the change of temperature $\Delta T$ over time in tissue when pulsatile RF power is applied to an electrode, in accordance with an embodiment of the invention. The change in temperature $\Delta T$ is cyclical, lagging each pulse and returning to a baseline prior to a subsequent pulse. The $\Delta T$ cycle and the temperature itself can be optimized suitably adjusting the frequency of the pulses and the power levels. Thus, the actual temperature in the myocardium can be maintained within desired limits, which allow for a sufficiently strong signal to reliably calculate tissue thickness, but not so strong as to damage the myocardium.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising:
bringing an electrode that is disposed on a distal portion of a catheter to contact tissue, wherein the electrode has an area that falls within a range of 0.01-25 mm$^2$;
using the electrode to apply pulses of radiofrequency power to the tissue, the pulses having a width of between 10 μs and 100 μs;
recording temperatures at the distal portion while applying the pulses;
in response to the recorded temperatures, computing a rate of change of the temperatures at the distal portion;
estimating a thickness of the tissue in response to the rate of change, resulting in an estimated thickness of the tissue; and
in response to the estimated thickness of the tissue, estimating power to be used for ablation of the tissue and a time period over which the power is to be applied, in order to achieve the ablation of the tissue, wherein the method comprises the following steps:
performing a preparatory step performed before a start of the ablation of the tissue, wherein a relationship between the thickness of the tissue and a normalized rate of temperature change
of the distal portion is determined;
while bringing the electrode that is disposed on the distal portion of the catheter to contact the tissue, employing a force module and a processor, recording a contact force, wherein the contact force is sensed by a force sensor, setting a flow rate of irrigation to the distal portion, wherein a value for flow rate is set within a range 10-20 mL/min, wherein, while the distal end and the tissue are being irrigated, the processor uses the electrode to apply the pulses of radiofrequency power to the tissue in contact with the distal portion, wherein the processor sets the pulse to have a power of 30 Watts and a duration of 1 second, wherein the processor records values of flow rate, power, and duration,
performing a slope measurement step, wherein once the pulse has been applied to the tissue, the processor begins the recording of the temperatures, as well as times of recordation, wherein from the temperatures and the times, the processor evaluates a value of a slope and from the slope, the processor calculates the normalized rate of temperature change
said normalized rate of temperature change being the normalized slope of a corresponding temperature-time graph of the distal portion,
performing a tissue thickness step, wherein the processor applies the normalized slope found in the slope measurement step to data obtained in the preparatory step to estimate the thickness of the tissue, and
performing the ablation, wherein the processor employs the estimated tissue thickness in the estimating of the power to be used for the ablation of the tissue and the time period over which the power is to be applied.

2. The method according to claim 1, wherein the area of the electrode does not exceed 2.8 mm$^2$.

3. The method according to claim 1, wherein recording temperatures is performed at times corresponding to terminations of the pulses.

4. The method according to claim 1, wherein the width of the pulses is 100 μs.

5. The method of claim 1, wherein the pulses are iterated 10 times per second at a power level of 10 W per mm$^2$ of electrode area.

6. The method of claim 1, wherein the estimating of the power to be used for the ablation of the tissue and the time period over which the power is to be applied, uses an ablation index.

7. An apparatus, comprising:
a catheter having a distal portion;
an electrode disposed on the distal portion, wherein the electrode has an area that falls within a range of 0.01-25 mm$^2$;
a power generator connected to the electrode and configured to apply pulses of radiofrequency power to tissue in contact with the electrode, the pulses having a width of between 10 μs and 100 μs;
a temperature sensor at the distal portion for recording temperatures while the pulses are being applied; and
a processor operative for computing a rate of change of the temperatures at the distal portion in response to the recorded temperatures and for estimating a thickness of the tissue in response to the rate of change, resulting in an estimated thickness of the tissue;
the processor further operative for computing, in response to the estimated thickness of the tissue, estimated power to be used for ablation of the tissue and a time period over which the power is to be applied, in order to achieve the ablation of the tissue, wherein the apparatus is adapted to be employed in a method comprising the following steps:
performing a preparatory step performed before a start of the ablation of the tissue, wherein a relationship between the thickness of the tissue and a normalized rate of temperature change
of the distal portion is determined;
inserting the distal portion to contact a selected portion of the tissue, and, employing a force module and the processor, recording a contact force, wherein the contact force is sensed by a force sensor, setting a flow rate of irrigation to the distal portion, wherein a value for flow rate is set within a range 10-20 mL/min, wherein, while the distal end and the tissue are being irrigated, the processor uses the electrode to apply the pulses of radiofrequency power to the tissue in contact with the distal portion, wherein the processor sets the pulse to have a power of 30 Watts and a duration of 1 second, wherein the processor records values of flow rate, power, and duration,
performing a slope measurement step, wherein once the pulse has been applied to the tissue, the processor begins the recording of the temperatures, as well as times of recordation, wherein from the temperatures and the times, the processor evaluates a value of a slope and from the slope, the processor calculates the normalized rate of temperature change
said normalized rate of temperature change being the normalized slope of a corresponding temperature-time graph of the distal portion,
performing a tissue thickness step, wherein the processor applies the normalized slope found in the slope measurement step to data obtained in the preparatory step to estimate the thickness of the tissue, and performing the ablation, wherein the processor employs the estimated tissue thickness in the estimating of the power to be used for the ablation of the tissue and the time period over which the power is to be applied.

8. The apparatus according to claim 7, wherein the area of the electrode does not exceed 2.8 mm².

9. The apparatus according to claim 7, wherein the processor is operative for recording temperatures at times corresponding to terminations of the pulses.

10. The apparatus according to claim 7, wherein the width of the pulses is 100 μs.

11. The apparatus of claim 7, wherein the pulses are iterated 10 times per second at a power level of 10 W per mm² of electrode area.

12. The apparatus of claim 7, wherein the processor is configured to compute the estimated power to be used for the ablation of the tissue, and the time period over which the power is to be applied, using an ablation index.

* * * * *